United States Patent [19]
Gentle et al.

[11] Patent Number: 5,486,565
[45] Date of Patent: Jan. 23, 1996

[54] ORGANOSILICON COMPOUNDS AND LOW TEMPERATURE CURING ORGANOSILOXANE COMPOSITIONS CONTAINING SAME

[75] Inventors: Theresa E. Gentle; Michael A. Lutz, both of Midland, Mich.

[73] Assignee: Dow Corning Corporation, Midland, Mich.

[21] Appl. No.: 348,425

[22] Filed: Dec. 2, 1994

[51] Int. Cl.$^6$ .................................................. C08K 5/54
[52] U.S. Cl. .......................... 524/730; 528/29; 524/731; 556/434; 556/431; 556/443; 556/444; 556/450; 556/457
[58] Field of Search ................. 524/730, 731; 528/29; 556/434, 431, 443, 444, 450, 457

[56] References Cited

U.S. PATENT DOCUMENTS

| | | | |
|---|---|---|---|
| 2,349,338 | 5/1944 | Clapsadle et al. | 353/75 |
| 2,630,446 | 3/1953 | Gresham | 260/448.8 |
| 2,776,307 | 1/1957 | Ross et al. | 260/448.8 |
| 3,029,269 | 4/1962 | Abbott et al. | 260/448.8 |
| 3,772,026 | 11/1973 | Greenwald | 96/77 |
| 3,873,334 | 3/1975 | Lee et al. | 106/287 |
| 3,992,429 | 11/1976 | Knollmueller | 260/448.8 |
| 4,072,655 | 2/1978 | Louis et al. | 260/46.5 |
| 4,082,726 | 4/1978 | Mine et al. | 260/46.5 |
| 4,087,585 | 5/1978 | Schulz | 428/429 |
| 4,196,273 | 4/1980 | Imai et al. | 528/15 |
| 4,329,273 | 5/1982 | Hardman et al. | 524/862 |
| 4,659,851 | 4/1987 | Plueddemann | 556/431 |
| 4,719,262 | 1/1988 | Plueddemann | 525/105 |
| 4,732,932 | 3/1988 | Waldern | 524/862 |
| 5,106,933 | 4/1992 | Kobayashi et al. | 528/15 |
| 5,306,341 | 4/1994 | Ono et al. | 528/29 |

FOREIGN PATENT DOCUMENTS 450875  8/1920  United Kingdom ............ 3069 35

OTHER PUBLICATIONS

"The Preparation of Alkoysilanes From Glycols And Glycol Monoethers" H. G. Emblem and K. Hargreaves, Joseph Crosfield and Sons Ltd., Warrington. pp. 721 vol. 30 (3) 1968.

*Primary Examiner*—Melvyn I. Marquis
*Attorney, Agent, or Firm*—Robert Spector

[57] ABSTRACT

The present invention relates to organosiloxane compositions that are reaction products of 1) a silane containing at least 3 hydrolyzable groups per molecule, 2) a monohydric or polyhydric alcohol containing at least one organofunctional group and 3) a polyhydric alcohol containing no organofunctional groups or ethylenic unsaturation, wherein said reaction products contain at least two silicon atoms. The organosiloxane compositions are particularly useful as adhesion promoting additives for curable organosiloxane compositions, particularly those that cure by a platinum group metal-catalyzed hydrosilation reaction.

11 Claims, No Drawings

ORGANOSILICON COMPOUNDS AND LOW TEMPERATURE CURING ORGANOSILOXANE COMPOSITIONS CONTAINING SAME

BACKGROUND OF THE INVENTION

1. Field of the Invention

This invention relates to a novel class of organosilicon compounds. This invention also relates to organosiloxane compositions that cure by a platinum group metal catalyzed hydrosilation reaction and contain these compound as adhesion promoting additives. The compounds are particularly useful for achieving adhesion to a variety of substrates at curing temperatures below about 100° C.

2. Background Information

One type of curable organosiloxane composition comprises an organopolysiloxane containing ethylenically unsaturated organic groups and an organosilicon compound containing silicon-bonded hydrogen atoms, curable in the presence of a catalyst which comprises a group VIII metal or a compound or complex thereof. Usually, the catalyst is a compound or complex of platinum. Unfortunately, the adhesion of these type of compositions is generally poor, limiting their usefulness in many applications.

Several methods are known to improve the adhesion of organosiloxane compositions, however most generally have limitations. For example, primers can be used to improve the adhesion, but their use requires a separate processing step which increases process time and cost. Additionally, the primer usually requires a heat-activated cure to be effective. Adhesion additives, which are added directly to the composition to promote adhesion, have therefore received considerable attention.

Useful adhesion additives typically contain at least two functional groups. U.S. Pat. No. 3,772,026 and U.S. Pat. No. 3,873,334 teach acyloxy functional silanes which additionally contain silicon bonded hydrogen atoms or alkenyl radicals, respectively. Although the acyloxy functionality is very reactive, it liberates corrosive acetic acid upon reaction with hydroxyl groups present at the surface of the substrate or with upon contact with water.

U.S. Pat. No. 4,196,273 teaches use of unsaturated alkoxysilanes as adhesion additives, however, adhesion is not demonstrated at temperatures below 100° C. and only adhesion to glass is demonstrated at 100° C. U.S. Pat. No. 4,329,273 teaches use of partially hydrolyzed alkoxysilanes containing ethylenically unsaturated groups bonded to the silicon atom. While satisfactory curing of these compositions containing these adhesion additives was demonstrated at 100° C., the compositions did not cure at ambient laboratory temperatures.

U.S. Pat. No. 4,082,726 teaches using organosilicon compounds containing epoxy functional dialkoxysilyl groups and at least one alkenyl group or silicon-bonded hydrogen atom as adhesion additives. The exemplified compositions are cured at temperatures between 100°–200°C.

U.S. Pat. No. 4,087,585 teaches physical blends of epoxy functional alkoxysilanes with silanol functional fluids containing alkenyl functionality. Cure was obtained at elevated temperatures. Multifunctional organosilanes containing ethylenic unsaturation, epoxy functionality, and alkoxy functionality are taught in U.S. Pat. No. 4,732,932. U.S. Pat. No. 5,106,933 teaches use of mixtures of alkoxysilanes.

U.S. Pat. No. 4,659,851, U.S. Pat. No. 4,719,262, and U.S. Pat. No. 4,906,686 teach reaction products of 1) unsaturated alcohols and ethers derived from these alcohols and 2) alkoxysilanes. A shortcoming of these reaction products is that the resultant Sew-O-C bond between the unsaturated alcohol and alkoxysilane would be susceptible to hydrolysis to the extent that the adhesion may be decreased upon exposure to moisture.

Organosilicon compounds obtained from the reaction of polyhydric alcohols with compounds containing silicon-bonded hydrolyzable groups are known in the art. U.S. Pat. No. 2,349,338 teaches silicic acid esters of monohydric and polyhydric alcohols, including various glycol and glycerol silicate ester derivatives, are useful as corrosion prevention additives for heat transfer liquids. The corrosion prevention is afforded by the hydrolysis product of these compounds.

U.S. Pat. No. 2,776,307 claims silicon-containing esters of the type $(R^1O)_3Si(XR^2)_nOSi(OR^3)_3$, where X can be oxygen, and n has a value of 2, 3, or 4. The compounds are said to be useful as hydraulic fluids and other lubricant purposes.

U.S. Pat. No. 3,992,429 teaches novel alkoxysilane cluster compounds containing sterically hindered alkyl groups to improve hydrolytic stability. Intended uses include heat transfer fluids, hydraulic fluids, brake fluids, transmission fluids, and the like.

U.S. Pat. No. 2,630,446 teaches polymeric silicates prepared from tetraalkyl orthosilicates and polyhydric alcohols. The silicates are intended for use as plasticizers, lubricants, and hydraulic fluid additives.

U.S. Pat. No. 4,072,655 teaches reaction products of polyhydric alcohols and silanes containing from 1 to 4 hydrolyzable groups per molecule. The reaction products are used as non-slump additives for moisture curable organosiloxane compositions.

The preparation of alkoxysilanes from glycols and glycol monoethers is taught by H. G. Emblem and K. Hargreaves in the Journal of Inorganic Nuclear Chemistry, Vol. 30 (3), p. 721, 1968).

The preparation of esters derived from tetraalkyl orthosilicates and polyhydroxy alcohols by a transesterification reaction is described in British Patent No. 450,875.

U.S. Pat. No. 3,029,269 teaches compounds of the type $(RO)_3SiOCR'_2(CH_2)_nCR'_2-OSi(OR)_3$, where n is 0–16 and R' is H or a lower aliphatic radical, and R is a saturated aliphatic radical of 1–16 carbons. The compounds are suggested as lubricants and hydraulic fluids and in general show low pour point, good viscosity and viscosity index properties as well as hydrolytic stability.

Finally, Applicants' copending application Ser. No. 08/240,598 filed on May 10, 1944, U.S. Pat. No. 5,424,384 describes adhesion promoting additives for curable organosiloxane compositions that are reaction products of a polyhydric saturated alcohol with a silane or bis-silylalkane. The organosilicon reactant contains at least three alkoxy or enoloxy groups on each silicon atom.

One objective of this invention is to provide a class of novel organosiloxanes that are particularly useful as adhesion promoting additives in organosiloxane compositions, particularly those that cure by a platinum group metal catalyzed hydrosilation reaction at temperatures below about 100°C.

SUMMARY OF THE INVENTION

The objectives of the present invention are achieved by providing organosiloxane compositions that are reaction products of 1) a silane containing at least 3 hydrolyzable groups per molecule, 2) a monohydric or polyhydric alcohol containing at least one organofunctional group and 3) a polyhydric alcohol that is free of organofunctional groups.

The present reaction products preferably comprise molecules containing the $=SiOR^1OSi=$ group wherein $R^1$ represents an alkylene or hydroxyalkylene radical and the remaining valences of the silicon atoms are satisfied by hydrolyzable groups and at least one adhesion-promoting organofunctional group that is bonded to silicon through an oxygen atom. Examples of suitable organofunctional groups include but are not limited to alkenyl, epoxyalkyl, (meth)acryloxyalkyl, carboxyalkyl, aminoalkyl, amidoalkyl and mercaptoalkyl.

DETAILED DESCRIPTION OF THE INVENTION

The organosilicon compounds of the present invention are products of the reaction between 1) a polyhydric alcohol of the general formula $R^1(OH)_m$, 2) a mono- or polyhydric alcohol of the general formula $R^2(OH)_n$ and 3) a silane of the formula $R^3_pSiX_{4-p}$, wherein $R^1$ is a hydrocarbon radical having a valence of m and no organofunctional substituents, $R^2$ is an organic radical with a valence of n comprising carbon, hydrogen, and at least one organofunctional substituent, where said substituent is selected from the group consisting of $CH_2=CH-$, acryloxy, methacryloxy, epoxy, carboxy, amino, amido, acrylamido, methacrylamido and mercapto, $R^3$ is an unsubstituted or substituted monovalent hydrocarbon radical, X represents a hydrolyzable group, m is at least 2, n is at least 1, and p is 0 or 1, and wherein each molecule of said organosilicon compounds reaction products contains at least two silicon atoms.

This invention also provides curable organosiloxane compositions comprising (A) a curable polyorganosiloxane;

(B) a curing agent in an amount sufficient to cure said composition;

(C) a curing catalyst in an amount sufficient to promote curing of said composition; and (D) an organosilicon composition of the present invention as an adhesion promoting additive in an amount sufficient to achieve adhesion to a substrate in contact with said composition during curing thereof.

The Present Compounds

The characterizing feature of the average molecule in the reaction products that constitute the present organosilicon compositions is the presence of 1) at least two residues per molecule derived from a silane containing at least three silicon-bonded hydrolyzable groups, represented by X in formula 1, and an optional monovalent hydrocarbon radical or a monovalent organofunctional group, represented by $R^3$, that is bonded to silicon through carbon, 2) at least one residue derived from a monohydric or polyhydric alcohol containing an organofunctional group, and 3) at least one residue derived from a polyhydric alcohol that is free of ethylenic unsaturation or other organofunctional groups.

As used in the present specification, the term "monovalent hydrocarbon radical" includes but is not limited to alkyl containing from 1 to about 20 carbon atoms, such as methyl, ethyl, n-hexyl and n-dodecyl; cycloalkyl such as cyclohexyl; aryl radicals such as phenyl and naphthyl; aralkyl such as benzyl and alkaryl such as tolyl and xylyl. These hydrocarbon radicals can be unsubstituted or contain non-reactive substituents such as halogen, or an organofunctional group.

The organofunctional group present on the hydrocarbon radical represented by $R^2$ reacts during curing of compositions containing the present reaction products as adhesion promoting additives. These organofunctional groups contain carbon, hydrogen and, when the organofunctional group is other than alkenyl, at least one of oxygen, nitrogen and sulfur.

The optional hydrocarbon radical $R^3$ on the silane reactant can be unsubstituted or can contain inert or organofunctional substituents. Inert substituents such as halogen atoms do not react during preparation of the present reaction products or during use of these reaction products in curable organosiloxane compositions.

When the compounds of this invention are present as the adhesion-promoting additives in a curable organosiloxane composition, the organofunctional groups react with at least one of the groups that either participate in the curing reaction of the organosiloxane composition or are present on a substrate that the composition is in contact with during curing.

Examples of suitable organofunctional groups include but are not limited to $CH_2=CH-$, epoxyalkyl, (meth)acryloxyalkyl, mercaptoalkyl, carboxyalkyl, amidoalkyl and aminoalkyl.

The present compounds will be referred to hereinafter as ingredient D of curable compositions containing these compounds as adhesion-promoting additives.

The hydrolyzable and organofunctional groups present in ingredient D can be any that will not interfere with curing of compositions containing this ingredient.

Examples of suitable hydrolyzable groups that can be represented by X in the formula for the silane reactant include but are not limited to alkoxy, enoloxy and ketoximo.

The present reaction products can be used as adhesion promoting additives in organosiloxane compositions that cure using any of the reactions known for these compositions. Examples of known curing reactions include but are not limited to the following:

hydrosilation reactions catalyzed by platinum group metals and compounds of these metals;

reactions of silicon-bonded hydrogen atoms with silanol groups catalyzed by platinum group metals, compounds of these metals, tin compounds or amines;

reactions of silanol groups with silicon-bonded hydrolyzable groups such as alkoxy and ketoximo that occur in the presence of atmospheric moisture and, optionally, a catalyst such as organotin and organotitanium compounds; and cationic or free radical reactions initiated by the decomposition of photolyrically unstable compounds or by exposure to high energy radiation.

As used in this specification the term "cure" means the conversion of a liquid or semi-solid composition to a crosslinked elastomeric or resinous material by the reaction of groups present on the polyorganosiloxane referred to as ingredient A of the present compositions with the curing agent.

The present adhesion-promoting additives are preferably used with organosiloxane compositions that cure by a hydrosilation reaction catalyzed by metals from the platinum group of the periodic table and compounds of these metals. The additives are particularly useful in compositions that are cured at temperatures up to 100° C.

During formation of preferred embodiments of the present adhesion additives, one alkoxy or other hydrolyzable group per molecule of the silane $R^3{}_pSiX_{4-p}$ reacts with a hydroxyl group on the polyhydric alcohol $R^1(OH)_m$ and a second hydrolyzable group of the silane reacts with a hydroxyl group of the organofunctional alcohol $R^2(OH)_n$. Preferably at least 50 percent, most preferably at least 90 percent of the initial silane molecules react with both the organofunctional alcohol and the polyhydric alcohol $R^1(OH)_m$ and the polyhydric alcohol reacts with 2 molecules of silane.

It is possible for two or more alkoxy or other hydrolyzable groups on the initial silane to react with the same or different molecules of the polyhydric alcohol $R^1(OH)_m$. Alternatively, a given molecule of the silane can react with 0, 1, 2 or 3 moles of the organofunctional alcohol $R^2(OH)_n$. Other possible reaction products will be apparent to those knowledgeable in the equilibration reactions of silanes containing hydrolyzable groups with two different alcohols.

The present reaction products are typically mixtures of the various possible products. When the polyhydric alcohol $R^1(OH)_m$ is a diol, using the preferred molar ratio of silane:polyhydric alcohol:organofunctional alcohol of 1.4:1:1, the major portion of the reaction product should contain one residue from each of the two types of alcohols. A larger relative concentration of silane will be required when m in the formula for the unsubstituted polyhydric alcohol is 3.

The silane used to prepare the present reaction products is represented by the formula $R^3{}_nSiX_{4-n}$, wherein $R^3$ represents a monovalent hydrocarbon radical that can be substituted or unsubstituted. When $R^3$ contains a substituent, it can be relatively inert, such as a halogen atom, or it can be an organofunctional group. Suitable organofunctional groups are discussed in a preceding section of this specification.

Preferred silane reactants that do not contain organofunctional groups include but are not limited to methyltrimethoxysilane, methyltriethoxysilane, tetramethyl orthosilicate and tetraethyl orthosilicate. methyltriisopropenyloxysilane. Examples of silanes containing organofunctional groups include but are not limited to vinyltrimethoxysilane, 3-methacryloxypropyltrimethoxysilane and 3-glycidoxypropyltrimethoxysilane.

The polyhydric alcohol $R^1(OH)_m$ contains from 2 to 20 or more carbon atoms and is free of ethylenic unsaturation or other organofunctional groups. Preferred polyhydric alcohols contain from 2 to 10 carbon atoms, two or three hydroxyl groups and include but are not limited to ethylene glycol, propylene glycol, 1,3-propanediol, glycerol, 1,4-butanediol, neopentyl glycol, 2,2,2-trimethylolpropane, and 1,10-decanediol. In preferred embodiments of the polyfunctional alcohol $R^1$ is an unsubstituted aliphatic radical containing from 2 to 5 carbon atoms and having a valence of m wherein m is 2 or 3.

When the number of hydroxyl groups in the polyhydric alcohol exceeds the number represented by m in formula 1, at lease a portion of the additional hydroxyl groups can be etherified or esterified.

The organofunctional alcohol represented by the formula $R^2(OH)_n$ contains from 3 to 20 or more carbon atoms and at least one of the organofunctional groups described in a preceding section of this specification. In preferred embodiments $R^2$ is an alkenyl radical containing from 3 to 12 carbon atoms. Examples of preferred alcohols are allyl alcohol, 3-buten-1-ol, 5-hexen-1-ol, 1-octene-3-ol and 10-undecen-1-ol.

A second class of suitable ethylenically unsaturated monohydric alcohols are half esters of dihydric alcohols wherein the acid portion of the ester is derived from an ethylenically unsaturated monocarboxylic acid such as acrylic or methacrylic acid. Examples of suitable esters of this type are ethylene glycol monoacrylate, propylene glycol monoacrylate and ethylene glycol monomethacrylate.

Silanes derived from other classes of ethylenically unsaturated monohydric organic compounds are described in U.S. Pat No. 4,719,262, which issued to Edwin Plueddemann on Jan. 12, 1988. The entire portion of this patent is incorporated into this specification by reference as a disclosure of the types of silanes useful as starting materials for preparing preferred embodiments of the present compounds.

The reaction between the polyhydric alcohol $R^1(OH)_m$, the organofunctional alcohol $R^2(OH)_n$ and the silane $R^3{}_pSiX_{(4-p)}$ is conducted under conditions that are typical for interchange reactions between alcohols and silicon-bonded hydrolyzable groups. These reactions are typically conducted under an inert, anhydrous atmosphere such as nitrogen at temperatures from ambient to 200° C. and may employ a catalyst such as an organotitanium compound. Suitable organotitanium compounds include but are not limited to tetraalkyl titanates such as tetraisopropyl titanate and tetra-n-butyl titanate and chelated organotitanium compounds such as 2,5-diisopropoxy-bis-ethylacetoacetate titanium.

The weight of catalyst typically constitutes from about 0.1 to about 5 percent of the combined weight of all reactants.

Reactions involving exchanges of silicon bonded alkoxy and enoloxy groups generate the alcohol or ketone corresponding to the original silicon-bonded alkoxy or enoloxy group as a by-product. Because these reactions are often reversible, it is usually desirable to remove this by-product alcohol or ketone by distillation as the reaction progresses.

The course of exchange reactions involving the generation and removal of alcohol and ketone by-products can readily be followed by measuring the amount of by-product collected.

Methanol and ethanol are the lowest boiling alcohols, and are most easily removed during preparation of the present adhesion-promoting additives. It is therefore preferable that the alkoxy groups of the present adhesion additives, represented by $OR^4$ in the foregoing formulae, be methoxy or ethoxy. For the same reason, the enoloxy group is preferably isopropenyloxy.

The reactants and optional catalyst are heated for a period of time sufficient to achieve a substantially complete reaction, as indicated by the amount of by-product alcohol or ketone collected. This time period is typically from 1 to about 5 hours and the reaction mixture is preferably heated from about 50° to 200° C.

It may be desirable to include in the reaction mixture a liquid diluent that may also function as a solvent for the reactants. Suitable diluents include aliphatic and aromatic hydrocarbons that are liquid at ambient temperature and boil within the range of from 50° to about 200° C. Representative diluents include alcohols such as methanol, ethanol, and isopropanol, aliphatic hydrocarbons such as hexane and heptane, and liquid aromatic hydrocarbons such as toluene and xylene.

The present organosilicon compositions can be prepared in two stages. During the first stage the polyhydric alcohol $R^1(OH)_m$ is reacted with the silane $R^3{}_pSiX_{4-p}$. The resultant reaction product is then blended with a curable organosiloxane composition, at which time the organofunctional alcohol $R^2(OH)_n$ is added to the composition. The present organosilicon composition is formed during curing of the organosiloxane composition.

The present adhesion promoting additives are particularly useful in organosiloxane compositions that cure by a platinum group metal-catalyzed hydrosilation reaction at temperatures below about 100° C.

The concentration of adhesion promoting ingredient D is sufficient to provide cohesive bonding of the cured composition to the desired substrate. This typically requires at least about 0.25 weight percent by weight of the adhesion promoter, based on the weight of the curable composition. A concentration of between 0.5 and 5 weight percent is preferred.

The ability of the organosiloxane composition to cure completely under the desired conditions and/or the properties of the cured composition can be adversely affected when the concentration of adhesion promoting additive exceeds about 10 weight percent, based on the weight of the curable composition.

For purposes of the present invention, cohesive bonding is characterized by cohesive failure, which occurs when the strength of the bond between the cured organosiloxane material and the substrate exceeds the tensile strength of the cured material. In a typical adhesion test increasing force is applied to the layer of cured material until it is removed from the substrate.

Cohesive failure occurs within the body of the cured organosiloxane material rather than at the interface between the material and the substrate that the material is in contact with during the curing reaction. At least a portion of the cured material remains adhered to the substrate. The degree of cohesive failure can be expressed as the level of force required to remove cured organosiloxane composition from a substrate that it is in contact with during the curing reaction.

The ingredients of preferred curable organosiloxane compositions suitable for use with the present adhesion promoting additives will now be discussed in detail.

The Polyorganosiloxane (Ingredient A)

The polyorganosiloxane ingredient, referred to hereinafter as ingredient A, of preferred curable organosiloxane compositions of this invention is the principal ingredient of these compositions. Because these compositions cure by a hydrosilation reaction, ingredient A contains at least two silicon-bonded alkenyl radicals in each molecule.

Suitable alkenyl radicals contain from 1 to about 10 carbon atoms and are exemplified by but not limited to vinyl, allyl and 5-hexenyl. The silicon-bonded organic groups other than alkenyl radicals present in ingredient A are typically monovalent hydrocarbon and halogenated monovalent hydrocarbon radicals exemplified by but not limited to alkyl radicals such as methyl, ethyl and propyl; aryl radicals such as phenyl; and halogenated alkyl radicals such as 3,3,3-trifluoropropyl.

The molecular structure of ingredient A is not critical to the present invention, and will be determined by the physical properties desired in the cured composition. To achieve a useful level of tensile properties in the elastomers and other products prepared by curing the present compositions, the molecular weight of this ingredient should be sufficient to achieve a viscosity at 25°C. greater than about 0.1 Pa.s.

The upper limit for the molecular weight of ingredient A is not specifically restricted, and is typically limited only by the processability of the curable organosiloxane composition. The polyorganosiloxanes range from pourable liquids to gum type polymers that are typically characterized by Williams plasticity values.

Preferred embodiments of ingredient A are polydiorganosiloxanes represented by the general formula I

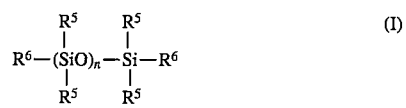

where each $R^5$ is individually selected from monovalent hydrocarbon radicals, $R^6$ represents a vinyl or other alkenyl radical, and n represents a degree of polymerization equivalent to a viscosity of am least 100 centipoise (0.1 Pa.s), preferably from 0.1 to 10 Pa.s.

The hydrocarbon radicals represented by $R^5$ are either unsubstituted or can contain substituents such as halogen atoms that will not adversely affect the storage stability and curing of the present compositions or the properties of cured articles prepared from these compositions.

The two $R^5$ substituents on each of the silicon atoms in formula I can be identical or different, and can contain from 1 to about 20 carbon atoms. A range of from 1 to 10 carbon atoms is preferred based on the availability of the corresponding monomers. Most preferably at least one of the hydrocarbon radicals on each silicon atom is methyl, and any remainder are vinyl, phenyl and/or 3,3,3-trifluoropropyl, this preference being based on the availability of the reactants typically used to prepare the polydiorganosiloxane and the properties of cured elastomers prepared from these polydiorganosiloxanes. For the same reasons, $R^6$ is preferably vinyl or 5-hexenyl.

Representative embodiments of ingredient A containing ethylenically unsaturated hydrocarbon radicals only at the terminal positions include but are not limited to dimethylvinylsiloxy-terminated polydimethylsiloxanes, dimethylvinylsiloxy-terminated polymethyl-3,3,3-trifluoropropylsiloxanes, dimethylvinylsiloxy-terminated-dimethylsiloxane/3,3,3-trifluoropropylmethylsiloxane copolymers and dimethylvinylsiloxy-terminated dimethylsiloxane/methylphenylsiloxane copolymers.

Methods for preparing ingredient A of the present compositions by hydrolysis and condensation of the corresponding halosilanes or by condensation of the cyclic polydiorganosiloxanes are sufficiently disclosed in the patent and other literature that a detailed description in this specification is not necessary.

For applications requiring high levels of physical properties such as tear strength it may be desirable to include in the curable organosiloxane composition a second polydiorganosiloxane containing ethylenically unsaturated hydrocarbon radicals bonded to both terminal and non-terminal silicon atoms.

The Organohydrogensiloxane Curing Agent (Ingredient B)

The preferred curable organosiloxane compositions of this invention contain at least one organohydrogensiloxane that functions as a curing agent for ingredient A. In the presence of the hydrosilation catalyst, referred to as ingredient C, the silicon-bonded hydrogen atoms in ingredient B undergo an addition reaction, referred to as hydrosilation, with the silicon-bonded alkenyl groups in ingredient A, resulting in crosslinking and curing of the composition.

Ingredient B must contain at least 2 silicon-bonded hydrogen atoms in each molecule. If ingredient A contains only two alkenyl radicals per molecule, ingredient B must contain an average of more than two silicon-bonded hydrogen atoms to achieve a crosslinked structure in the final cured product.

The silicon-bonded organic groups present in ingredient B are selected from the same group of monovalent hydrocarbon and halogenated hydrocarbon radicals as the organic groups of ingredient A. The organic groups in ingredient B are preferably substantially free of ethylenic or acetylenic unsaturation. The molecular structure of ingredient B can be straight chain, branch-containing straight chain, cyclic, or network.

While the molecular weight of ingredient B is not specifically restricted, viscosities in the range of 3 to 10,000 centipoise (0.003 to 10 Pa.s) at 25 degrees Centigrade are preferred.

The concentration of ingredient B is sufficient to provide a molar ratio of silicon-bonded hydrogen atoms to alkenyl radicals in the curable composition of from 0.5 to 20. A range of from 0.5 to 2 is preferred.

When the curable composition contains less than 0.5 moles of silicon-bonded hydrogen atoms per mole of alkenyl radicals it may not be possible to achieve the desired physical properties following curing. The physical properties of the cured article may vary with time when this ratio exceeds about 20 moles of silicon-bonded hydrogen per mole of alkenyl radicals.

The Platinum-Containing Hydrosilation Reaction Catalyst (Ingredient C)

Curing of the present compositions is catalyzed by a hydrosilation catalyst that is a metal from the platinum group of the periodic table or a compound of such a metal. These metals include platinum, palladium and rhodium. Platinum and platinum compounds are preferred based on the high activity level of these catalysts in hydrosilation reactions.

Examples of preferred curing catalysts include but are not limited to platinum black, platinum metal on various solid supports, chloroplatinic acid, alcohol solutions of chloroplatinic acid, and complexes of chloroplatinic acid with liquid ethylenically unsaturated compounds such as olefins and organosiloxanes containing ethylenically unsaturated hydrocarbon radicals bonded to silicon. Complexes of chloroplatinic acid with the aforementioned organosiloxanes containing ethylenically unsaturated hydrocarbon radicals are described in U.S. Pat. No. 3,419,593, which issued to David N. Willing on Dec. 31, 1968. The relevant portions of this patent are incorporated herein by reference as a teaching of preferred catalysts.

The concentration of ingredient C in the present compositions is equivalent to a platinum concentration of from 0.1 to 500 parts by weight of platinum metal, preferably from 1 to 50 parts by weight of platinum metal, per million parts (ppm), based on the combined weight of ingredients A and B.

Curing does not proceed satisfactorily at below 0.1 ppm of platinum, while using more than 500 ppm results in no appreciable increase in cure rate, and is therefore uneconomical.

Platinum Catalyst Inhibitor

Mixtures of the aforementioned ingredients A, B and C may begin to cure at ambient temperature. To obtain a longer working time or "pot life", the activity of the catalyst under ambient conditions can be retarded or suppressed by addition of a suitable inhibitor.

Known platinum catalyst inhibitors include the acetylenic compounds disclosed in U.S. Pat. No. 3,445,420, which issued on May 20, 1969 to Kookootsedes et al. Acetylenic alcohols such as 2-methyl-3-butyn-2-ol constitute a preferred class of inhibitors that will suppress the activity of a platinum-containing catalyst at 25°C. Compositions containing these catalyst inhibitors typically require heating at temperatures of 70° C. or above to cure at a practical rate.

When it is desired to increase the pot life of a curable composition under ambient conditions, this can be accomplished using an alkenyl substituted siloxane of the type described in U.S. Pat. No. 3,989,667, which issued on Nov. 2, 1976 to Lee and Marko. Cyclic methylvinylsiloxanes are preferred.

Inhibitor concentrations as low as one mole of inhibitor per mole of platinum will in some instances impart satisfactory storage stability and cure rate. In other instances inhibitor concentrations of up to 500 or more moles of inhibitor per mole of platinum are required. The optimum concentration for a given inhibitor in a given composition can readily be determined by routine experimentation and does not constitute part of this invention.

When it is desired to store for an extended period of time a one part composition that cures by a hydrosilation reaction and contains a platinum group metal or compound thereof as the catalyst, this can be achieved by encapsulating a finely divided form of the catalyst in a thermoplastic polymer that melts at the desired curing temperature. Encapsulated platinum-containing catalysts are described in U.S. Pat. No. 4,766,176 that issued on Aug. 23, 1988.

Alternative Curable Organosiloxane Compositions

In place of the polyorganosiloxane, curing agent and catalysts referred to in the preceding section of this specification as ingredients A, B and C, one type of alternative organosiloxane composition suitable for use with the present adhesion promoting additives contains a polyorganosiloxane with at least two silanol groups per molecule, an organosilicon compound containing at least three silicon-bonded hydrolyzable groups or silicon-bonded hydrogen atoms as the curing agent and an optional curing catalyst.

Suitable hydrolyzable groups for moisture curable compositions include but are not limited to alkoxy, enoloxy, ketoximo and carboxy such as acetoxy.

Other types of alternative composition cure by a free radical- or cationic polymerization initiated by the decomposition of a photolyrically unstable compound such as a alpha-hydroxy ketone or by high energy radiation, or by a free radical reaction initiated by thermal decomposition of a free radical precursor such as an organic peroxide or an azo compound.

Optional Ingredients

Reinforcing Fillers

To achieve high levels of tear strength and other physical properties that characterize some types of cured elastomers that can be prepared using the compositions of this invention, it may be desirable to include a reinforcing filler such as finely divided silica. Silica and other reinforcing fillers are often treated with one of more of the known filler treating agents to prevent a phenomenon referred to as "creping" or "crepe hardening" during processing of the curable composition.

Finely divided forms of silica are preferred reinforcing fillers. Fumed silicas are particularly preferred because of their relatively high surface area, which is typically at least 50 square meters per gram. Fillers having surface areas of at least 200 square meters per gram are preferred for use in the present method.

The amount of finely divided silica or other reinforcing filler used in the present compositions is at least in part determined by the physical properties desired in the cured elastomer. Liquid or pumpable polyorganosiloxane compositions typically contain from about 10 to about 60 percent by weight of silica, based on the weight of polydiorganosiloxane. This value is preferably from about 30 to about 50 percent.

The filler treating agent can be any of the low molecular weight organosilicon compounds disclosed in the art as being suitable for preventing creping of organosiloxane compositions during processing. The treating agents are typically liquid hydroxyl terminated polydiorganosiloxanes containing an average of from 2 to about 20 repeating units per molecule, and organosilicon compounds such as hexaorganodisiloxanes and hexaorganodisilazanes that hydrolyze and condense under the conditions used to treat the filler. Preferably at least a portion of the silicon bonded hydrocarbon radicals present on the treating agent are identical to a majority of the hydrocarbon radicals present in ingredients A and B. A small amount of water can be added together with the silica treating agent(s) as a processing aid.

It is believed that the treating agents function by reacting with silicon-bonded hydroxyl groups present on the surface of the silica or other filler particles to reduce interaction between these particles and the polyorganosiloxanes present in the curable composition.

When a silica filler is used, it is preferably treated in the presence of at least a portion of the other ingredients of the present compositions by blending these ingredients together until the filler is completely treated and uniformly dispersed to form a homogeneous material.

The ingredients that are present during treatment of the filler typically include the silica treating agents and at least a portion of the polydiorganosiloxane(s) referred to herein as ingredient A.

Additional Optional Ingredients

The present organosiloxane compositions can contain one or more additives that are conventionally present in curable compositions of this type to impart or enhance certain physical properties of the cured composition in addition to adhesion or to facilitate processing of the curable composition.

Typical additives include but are not limited to non-reinforcing fillers such as quartz, alumina, mica and calcium carbonate; pigments such as carbon black and titanium dioxide; dyes, flame retardants, and heat and/or ultraviolet light stabilizers. Resinous organosiloxane copolymers can be used in place of or in combination with one or more reinforcing fillers to improve the physical properties of the cured organosiloxane composition.

A preferred type of resinous copolymer contains repeating units of the general formula $SiO_{4/2}$ in addition to triorganosiloxy units of the general formulae $R^7_3SiO_{1/2}$ and diorganovinylsiloxy units of the general formula $CH_2=CH(R^8)_2SiO_{1/2}$. In these formulae $R^7$ and $R^8$ are individually monovalent hydrocarbon or substituted monovalent hydrocarbon radicals as previously defined for the $R^5$ radicals of ingredient A.

The molar ratio of the combination of triorganosiloxy units and diorganovinylsiloxy units to $SiO_{4/2}$ units in the resinous copolymer is from 0.7 to 1.2, inclusive. The vinyl-containing units constitute from 2 to 8 percent by weight of the copolymer, which preferably contains at least two vinyl radicals per molecule. In preferred embodiments of the copolymer the ranges for the molar ratio of diorganovinylsiloxy:triorganosiloxy:$SiO_{4/2}$ units is 0.08–0.1:0.06–1:1.

The resinous copolymers can be prepared as described in U.S. Pat. No. 2,676,182, which issued to Daudt and Tyler on Apr. 20, 1954 and is hereby incorporated in this specification by reference thereto to teach the preparation of and the scope of these resins. The copolymers described in this patent contain from 2 to 23 percent by weight of hydroxyl groups, which is considerably above the maximum level of about 0.8 weight percent preferred for precursors of the present copolymers. The hydroxyl content of the precursor can be conveniently reduced to the desired level by employing a higher concentration of triorganosiloxy units than the concentration range taught by Daudt et al.

Preparation of Curable Compositions

The compositions of this invention can be prepared by combining all of ingredients at ambient temperature. Any of the mixing techniques and devices described in the prior art can be used for this purpose. The particular device used will be determined by the viscosity of the ingredients and the final curable composition. Suitable mixers include but are not limited to paddle type mixers, kneader type mixers and two- and three-roll rubber mills.

Cooling of the ingredients during mixing may be desirable to avoid premature curing of the composition.

To maximize storage stability of preferred organosiloxane compositions that cure by a hydrosilation reaction, these compositions are preferably kept in closed containers until used. If greater storage stability is desired, the compositions can be packaged in two or more containers with the organohydrogensiloxane (ingredient B) and the platinum group metal catalyst (ingredient C) in different containers.

Depending upon the types and concentrations of ingredients A and B, cured organosiloxane materials prepared using the present compositions can vary in properties from brittle resins to elastomers to gels, and are useful in a variety of end-use applications as coatings or as molded or extruded articles.

Unfilled curable organosiloxane compositions are particularly useful as adhesives, protective coatings, encapsulants and potting compositions for protecting delicate electronic devices such as transistors and integrated circuits from damage by moisture and other materials present in the environment that can adversely affect operation of the device. The compositions can be used to coat either the individual devices or a circuit board containing a number of these devices together with other electronic components.

The present compositions can be applied to substrates by spraying, dipping, pouring, extrusion or by the use of a brush, roller or coating bar. The selection of a particular application method will be determined at least in part by the viscosity of the curable composition. The viscosity of the composition can be reduced using suitable solvents or reactive diluents as known in the art.

Organosiloxane compositions containing the present adhesion additives cohesively bond to a variety of organic and inorganic substrates during curing at temperatures as low as 25° C. The ability of the present compositions to develop adhesion when cured at these relatively low temperatures make them suitable for application to substrates that cannot withstand the elevated temperatures of 100°C. or higher required to cure organosiloxane compositions containing prior art adhesion additives, some of which may inhibit platinum group metal catalysts.

Preferred compositions cure over a period of several hours under ambient conditions. As is true for other compositions that cure by a platinum-catalyzed hydrosilation reaction, curing can be accelerated by heating. Curing temperatures of from 25°to about 80°C. are preferred.

EXAMPLES

The following examples describe preferred curable compositions of the present invention and should not be interpreted as limiting the scope of the invention defined in the accompanying claims. Unless otherwise specified all parts and percentages in the example are by weight and viscosities were measured at 25° C.

The following general procedure was used to prepare the partial reaction products of polyhydric alcohols, monohydric alcohols, and alkoxysilanes:

The alkoxysilane and titanate catalyst were charged into a three-necked, round bottom glass reactor. The reactor was then equipped with a stirrer, thermometer, Thermo-Watch(R) temperature control, addition funnel, distillation head, condenser, receiver flask cooled with dry ice, and a dry ice-cooled cold finger trap. The reactor was then filled with nitrogen.

All the glassware had been fried at 120°C. prior to use. The addition funnel was charged with the polyol, an equal weight of ethyl alcohol, and the unsaturated alcohol. The reaction mixture was then stirred, heated to about 75°C., and the contents of the addition funnel added slowly. Following completion of the addition a stream of nitrogen was passed through the reactor and the reaction mixture was heated at about 105°C. until no additional liquid collected in the receiver, which generally required from 0.5 to 1.5 hours of heating. Heating was continued while the pressure in the reactor was rapidly reduced to about 40 mm Hg and maintained there for 20 minutes. The reaction mixture was then cooled and brought to atmospheric pressure. The recovered liquid under atmospheric pressure was primarily ethyl alcohol and a mixture of ethyl alcohol and tetraethyl orthosilicate under reduced pressure.

Preparation of Adhesion Additives

Adhesion additive D1 was prepared by reacting 64.21 parts of tetraethyl orthosilicate, 0.1 part of tetrabutyl titanate, 9.56 parts of anhydrous ethylene glycol, and 26.23 parts of undecylenyl alcohol. The polyol/monohydric alcohol solution was added over a 47 minute period and was then heated for 25 minutes before the vacuum was applied. 27.2 parts of distillate was collected prior to application of vacuum, which was shown to contain 91.6% ethyl alcohol and 8.4% tetraethyl orthosilicate by gas/liquid chromatography (GC).

Following application of vacuum, 6.04 parts distillate was collected which was shown to contain 60.1% ethyl alcohol and 39.8% tetraethyl orthosilicate by GC analysis. The product (72.6 parts) was a transparent yellow/brown fluid.

Adhesion additive D2c is outside the scope of the present invention, and was prepared for comparative purposes by reacting tetraethyl orthosilicate (245.6 parts), tetrabutyl titanate (0.45 parts), and undecylenyl alcohol (199.6 parts). No polyol or ethyl alcohol was used in this adhesion additive.

The unsaturated alcohol was added over about an 8 hour period at a temperature of about 95° C., at which time the reaction mixture was heated to a final temperature of 140°C. Removal of volatile liquids under reduced pressure was not used in this preparation.

Tetraethyl orthosilicate (TEOS) and ethyl polysilicate (EPS) were also used as adhesion additives for comparative purposes.

Each of the curable compositions contained tetrabutyl titanate (TBT) as a catalyst to increase the rate of adhesion development.

The two part curable organosiloxane composition used to evaluate the adhesion promoters contained the following ingredients:

Part A 46 parts of a dimethylvinylsiloxy-terminated polydimethylsiloxane having a viscosity of about 0.4 Pa.s at 25° C. 46 parts of quartz having an average particle size of 5 microns; 7 parts of a dispersion containing 80 weight percent of a dimethylvinylsiloxy-terminated polydimethylsiloxane having a viscosity of about 0.4 Pa.s at 25° C., 13 weight percent zinc oxide and 7 weight percent lampblack; and 0.2 part of a reaction product of hexachloroplatinic acid and sym-tetramethyldivinyldisiloxane that has been diluted with a liquid dimethylvinylsiloxy terminated polydimethylsiloxane in an amount sufficient to achieve a platinum content of 0.7 weight percent.

Part B 47 parts of a dimethylvinylsiloxy-terminated polydimethylsiloxane exhibiting a viscosity of about 0.4 Pa.s at 25°C. (Ingredient A) 47 parts of quartz having an average particle size of 5 microns; 6 parts of a trimethylsiloxy-terminated polydiorganosiloxane containing an average of five methylhydrogensiloxane units and three dimethylsiloxane units per molecule with a silicon-bonded hydrogen atom content in the range from about 0.7 to 0.8 weight percent (Ingredient B), and 0.1 part of cyclic methylvinylsiloxanes.

Some of the compositions contained additional quantities of the organohydrogensiloxane (Ingredient B).

The amounts of parts A and B of the curable composition and the type and amounts of adhesion promoter used to prepare each of the compositions evaluated are summarized in Tables 1 and 2. The amount are expressed as parts by weight.

TABLE 1

| Composition[1] | C1 | C2 | C3 | C4 | C5 | C6 |
|---|---|---|---|---|---|---|
| Part A | 7.5 | 7.5 | 7.5 | 7.5 | 4.88 | 4.76 |
| Part B | 7.5 | 7.5 | 7.5 | 7.5 | 4.89 | 4.75 |
| TBT | 0.015 | 0.015 | 0.015 | 0.015 | 0.010 | 0.010 |
| Ingredient D | | | | | | |
| Type | EPS | EPS | TEOS | TEOS | D2c | D2c |
| Concentration | 0.38 | 0.75 | 0.38 | 0.75 | 0.23 | 0.43 |
| Ingredient B | 0.00 | 0.00 | 0.00 | 0.00 | 0.09 | 0.17 |

[1]= Concentrations in parts by weight
Compositions C1 through C6 were for comparative purposes.

TABLE 2

| Composition (Pts.) | 1 | 2 | 3 | 4 |
|---|---|---|---|---|
| Part A | 4.89 | 4.88 | 4.75 | 4.74 |
| Part B | 4.89 | 4.90 | 4.79 | 4.76 |
| TBT | 0.010 | 0.010 | 0.010 | 0.010 |
| Additive Type | D1 | D1 | D1 | D1 |
| Additive Conc. | 0.25 | 0.33 | 0.51 | 0.67 |
| Ingredient B | 0.07 | 0.09 | 0.13 | 0.17 |

After being placed under reduced pressure to remove entrapped air bubbles, portions of each sample were drawn down as 0.008 inch (0.2 mm)-thick liquid films onto a substrate.

The substrates on which the curable compositions were evaluated were glass microscope slides (glass), panels measuring 7.6 by 12.7 cm. and formed from type 3003 H14 alloy mill finish aluminum available from Q-Panel (mill aluminum), type 2024 T3 bare aluminum panels measuring 2.5 by 7.6 cm. (bare aluminum), epoxy-bonded fiberglass panels measuring 7.6 by 12.7 cm., available as G-10 from Almac Plastics, Inc. (epoxy), and copper plated epoxide panels measuring 2.5 by 7.6 cm (copper).

The compositions were cured either at room temperature or for 30 minutes at 70° C. in a forced air oven followed by additional cure am room temperature.

The adhesion test consisted of scratching the cured coatings with the blade of a metal spatula to determine whether the coating could be removed without leaving a residue on the surface (adhesive failure, AF) or whether failure occurred within the coating layer, resulting in at least a portion of the coating material in the test area adhering to the substrate (cohesive failure, CF). On some samples the coating exhibited adhesive failure in some areas and cohesive failure in others (AF/CF).

Coatings exhibiting cohesive failure were further tested to determine if the residue on the substrate and the adjacent coating material could be removed by rubbing with a finger. If the coating could be removed in this manner, the pressure required to remove the coating was rated on a subjective scale as slight (WE), medium (WM) or high (WD).

The adhesion achieved for the coatings cured at room temperature and by heating are recorded in Tables 3 and 4.

TABLE 3

| | Room Temperature Adhesion | | | | | | | | | |
|---|---|---|---|---|---|---|---|---|---|---|
| | Glass | | Bare Aluminum | | Mill Aluminum | | Copper | | Epoxy | |
| Composition | 1 Day | 3 Days | 1 Day | 3 Days | 1 Day | 3 Days | 1 Day | 3 Days | 1 Day | 3 Days |
| C1 | CF | CF | AF | AF | AF/CF | CF | AF | AF | AF | AF |
| C2 | CF | CF | AF | AF | CF | CF | AF | AF | AF | AF |
| C3 | AF | AF | AF | AF | AF | AF/CF | AF | AF | AF | AF |
| C4 | AF | AF | AF | AF | AF | AF | AF | AF | AF | AF |
| C5 | CF | CF | CF | CF | CF | CF | WM | CF | AF | AF |
| C6 | CF | CF | CF | CF | CF | CF | AF | CF | AF | AF |
| 1 | CF | CF | CF | CF | CF | CF | WM | CF | AF | AF |
| 2 | CF | CF | CF | CF | CF | CF | WM | CF | AF | AF |
| 3 | CF | CF | CF | CF | CF | CF | WD | CF | AF | AF |
| 4 | CF | CF | CF | CF | CF | CF | WE | CF | WE | AF |

TABLE 4

| | Oven Cured Adhesion | | | | | | | | | |
|---|---|---|---|---|---|---|---|---|---|---|
| | Glass | | Bare Aluminum | | Mill Aluminum | | Copper | | Epoxy | |
| Composition | Initial | 1 Day | Initial | 1 Day | Initial | 1 Day | Initial | 1 Day | Initial | 1 Day |
| C1 | AF | CF | AF | AF | AF | AF | AF | AF | AF | AF |
| C2 | AF | CF | AF | AF | AF | AF | AF | AF | AF | AF |
| C3 | AF | AF | AF | AF | AF | AF | AF | AF | AF | AF |
| C4 | AF | AF | AF | AF | AF | AF | AF | AF | AF | AF |
| C5 | CF | CF | CF | CF | CF | CF | AF | AF | AF | AF |
| C6 | CF | CF | CF | CF | CF | CF | AF | AF | WE | AF |
| 1 | CF | CF | AF | CF | CF | CF | AF | CF | AF | AF |
| 2 | CF | CF | AF | CF | CF | CF | AF | AF | AF | AF |
| 3 | CF | CF | WE | CF | CF | CF | AF | AF | WE | WE |
| 4 | CF | CF | CF | CF | CF | CF | AF | CF | CF | CF |

The results summarized in Tables 3 and 4 demonstrate the excellent adhesion to a variety of substrates following curing at either room temperature or for a short period of time at 70° C. using compositions containing the adhesion promoting additives of the present invention.

That which is claimed is:

1. An organosilicon composition comprising at least one compound formed by the interchange reaction between 1) a polyhydric alcohol of the general formula $R^1(OH)_m$, 2) an alcohol of the general formula $R^2(OH)_n$ and 3) a silane of the formula $R^3_p SiX_{4-p}$, wherein $R^1$ is a hydrocarbon radical having a valence of m and no ethylenic unsaturation, $R^2$ is an organic radical having a valence of n and comprising carbon, hydrogen, and at least one organofunctional substituent selected from the group consisting of $CH_2=CH-$, acryloxy, methacryloxy, epoxy, carboxy, amino, amido, acrylamido, methacrylamido, and mercapto, $R^3$ is an unsubstituted or substituted monovalent hydrocarbon radical, X represents a hydrolyzable group, m is at least 2, n is at least 1, p is 0 or 1 and wherein each molecule of said compound contains at least two silicon atoms.

2. A composition according to claim 1 wherein $R^1$ contains from 2 to 20 carbon atoms; $R^2$ is a monovalent hydrocarbon radical containing said organofunctional substituent; $R^3$ is selected from the group consisting of alkyl, alkenyl, epoxyalkyl and methacryloxyalkyl; X represents an alkoxy or ketoximo group; m is 2 or 3 and n is 1, 2 or 3.

3. A composition according to claim 2 wherein $R^1$ contains from 2 to 10 carbon atoms, $R^2$ is an alkyl radical containing said organofunctional substituent, and X represents an alkoxy group containing from 1 to 4 carbon atoms.

4. A composition according to claim 3 wherein said silane is selected from the group consisting of methyltrimethoxysilane, methyltriethoxysilane, tetramethyl orthosilicate, tetraethyl orthosilicate, methyltriisopropenyloxysilane, vinyltrimethoxysilane, 3-methacryloxypropyltrimethoxysilane and 3-glycidoxypropyltrimethoxysilane; said polyhydric alcohol is selected from the group consisting of ethylene glycol, propylene glycol, 1,3-propanediol, glycerol, 1,4-butanediol, neopentyl glycol, 2,2,2-trimethylolpropane, and 1,10-decanediol; said alcohol represented by the formula $R^2(OH)_n$ is selected from the group consisting of allyl alcohol, 3-buten-1-ol, 5-hexen-1-ol, 1-octene-3-ol and 10-undecen-1-ol; and compound contains at least two silicon atoms.

5. A curable organosiloxane composition comprising
A. a curable polyorganosiloxane;
B. an amount of a curing agent sufficient to cure said composition;
C. an amount of a catalyst sufficient to promote curing of said composition; and
D. as an adhesion promoting additive, an organosilicon composition comprising at least one compound formed by the interchange reaction between 1) a polyhydric alcohol of the general formula $R^1(OH)_m$, 2) an alcohol of the general formula $R^2(OH)_n$ and 3) a silane of the formula $R^3_p SiX_{4-p}$, wherein $R^1$ is a hydrocarbon radical exhibiting a valence of m and free of ethylenic unsaturation, $R^2$ is an organic radical exhibiting a valence of n and comprising carbon, hydrogen, and at least one organofunctional substituent selected from the group consisting of $CH_2=CH-$, acryloxy, methacryloxy, epoxy, carboxy, amino, amido, acrylamido, methacrylamido, and mercapto, $R^3$ is an unsubstituted or substituted monovalent hydrocarbon radical, X represents a hydrolyzable group, m is at least 2, n is at least 1, and p is 0 or 1 and wherein each molecule said compound contains at least two silicon atoms.

6. A composition according to claim 5 wherein $R^1$ contains from 2 to 20 carbon atoms; $R^2$ is a monovalent hydrocarbon radical containing said organofunctional substituent; $R^3$ is selected from the group consisting of alkyl, alkenyl, epoxyalkyl and methacryloxyalkyl; X represents an alkoxy or ketoximo group; m is 2 or 3 and n is 1, 2 or 3.

7. A composition according to claim 6 wherein $R^1$ contains from 2 to 20 carbon atoms, $R^2$ is an alkyl radical containing said organofunctional substituent, $R^3$ is selected from the group consisting of alkyl, alkenyl, epoxyalkyl and methacryloxyalkyl, and X represents an alkoxy group containing from 1 to 4 carbon atoms, m is 2 or 3 and n is 1, 2 or 3.

8. A composition according to claim 7 wherein said said silane is selected from the group consisting of methyltrimethoxysilane, methyltriethoxysilane, tetramethyl orthosilicate, tetraethyl orthosilicate, methyltriisopropenyloxysilane, vinyltrimethoxysilane, 3-methacryloxypropyltrimethoxysilane and 3-glycidoxypropyltrimethoxysilane, said polyhydric alcohol is selected from the group consisting of ethylene glycol, propylene glycol, 1,3-propanediol, glycerol, 1,4-butanediol, neopentyl glycol, 2,2,2-trimethylolpropane, and 1,10-decanediol; said alcohol represented by the formula $R^2(OH)_n$ is selected from the group consisting of allyl alcohol, 3-buten-1-ol, 5-hexen-1-ol, 1-octene-3-ol and 10-undecen-1-ol; and compound contains at least two silicon atoms.

9. A composition according to claim 5 wherein said composition cures by a reaction selected from the group consisting of hydrosilation reactions catalyzed by platinum group metals and compounds thereof, the reaction of silanol groups with silicon-bonded hydrolyzable groups in the presence of moisture, the reaction of silicon-bonded hydrogen atoms with silanol groups, the reaction of mercapto groups with one another in the presence of oxygen and a catalyst, the reaction of mercapto groups with alkenyl radicals in the presence of a catalyst, free radical and cationic reactions initiated by irradiation of photosensitive compounds with ultraviolet light, free radical reactions initiated by the thermally induced decomposition of a free radical precursor and reactions initiated by high energy radiation.

10. A composition according to claim 5 wherein said polyorganosiloxane exhibits a viscosity greater than 0.1 Pa.s at 25° C. and corresponds to the general formula

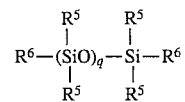

wherein each $R^5$ is individually selected from monovalent hydrocarbon radicals, $R^6$ represents an alkenyl radical, and q represents a degree of polymerization equivalent to a viscosity of at least 100 centipoise (0.1 Pa.s);

said curing agent is an organohydrogensiloxane exhibiting a viscosity at 25° C. of from 0.003 to 10 Pa.s;

the organic groups bonded to the silicon atoms of said organohydrogensiloxane are selected from the group consisting of monovalent unsubstituted and substituted hydrocarbon radicals;

the concentration of said organohydrogensiloxane is sufficient to provide a molar ratio of silicon-bonded hydrogen atoms to alkenyl radicals in said composition of from 0.5 to 2; and the curing catalyst is selected from the group consisting of platinum group metals and compounds of said metals and is present in said composition at a concentration equivalent to from 1 to 50 parts by weight of platinum group metal per million parts by weight of the combination of said polyorganosiloxane and said organohydrogensiloxane.

11. A composition according to claim 10 wherein q represents a degree of polymerization equivalent to a viscosity of from 0.1 to 10 Pa.s at 25° C. and said composition is packaged in at least two containers with said organohydrogensiloxane and said catalyst located in different containers.

* * * * *